(12) United States Patent
Karami et al.

(10) Patent No.: US 11,601,073 B2
(45) Date of Patent: Mar. 7, 2023

(54) PIEZOELECTRIC ENERGY HARVESTING USING A NONLINEAR BUCKLED BEAM AND METHOD FOR SAME

(71) Applicant: The Research Foundation for The State University of New York, Buffalo, NY (US)

(72) Inventors: Mohammad Amin Karami, Buffalo, NY (US); Mohammad Hossein Ansari, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 846 days.

(21) Appl. No.: 16/326,557

(22) PCT Filed: Aug. 21, 2017

(86) PCT No.: PCT/US2017/047872
§ 371 (c)(1),
(2) Date: Feb. 19, 2019

(87) PCT Pub. No.: WO2018/035542
PCT Pub. Date: Feb. 22, 2018

(65) Prior Publication Data
US 2019/0190404 A1     Jun. 20, 2019

Related U.S. Application Data

(60) Provisional application No. 62/377,221, filed on Aug. 19, 2016.

(51) Int. Cl.
*H02N 2/18*     (2006.01)
*H01L 41/08*     (2006.01)
(Continued)

(52) U.S. Cl.
CPC ........... *H02N 2/186* (2013.01); *A61N 1/3785* (2013.01); *H01L 41/00* (2013.01);
(Continued)

(58) Field of Classification Search
CPC ....... H02N 2/186; H02N 2/181; H01L 41/113
See application file for complete search history.

(56) References Cited

U.S. PATENT DOCUMENTS 6,313,568 B1    11/2001   Sullivan et al.
7,446,459 B2 *   11/2008   Xu ........................... H02N 2/18
                                                       310/330
(Continued)

FOREIGN PATENT DOCUMENTS

JP     2004146640 A    5/2004
JP     2007166881 A    6/2007
(Continued)

OTHER PUBLICATIONS

Sodano, H.A., et al., A Review of Power Harvesting from Vibration using Piezoelectric Materials, The Shock and Vibration Digest, May 2004, vol. 36, No. 3, pp. 179-205.

*Primary Examiner* — J. San Martin
(74) *Attorney, Agent, or Firm* — Hodgson Russ LLP

(57) ABSTRACT

An energy harvester includes a frame having a base, a first side member affixed to the base, and a second side member affixed to the base and spaced apart from the first side member. A beam is coupled between the first side member of the frame and the second side member of the frame. The beam has a substrate layer with a first end affixed to the first side member of the frame, a second end affixed to the second side member of the frame, a first face, and a second face opposite to the first face. The substrate is elastically deformable in response to the vibratory force. The beam further includes a first piezoelectric layer joined to the first face of the substrate layer and having a terminal for electrical (Continued)

connection to a load, the first piezoelectric layer comprising at least one piezoelectric patch.

19 Claims, 15 Drawing Sheets

(51) Int. Cl.
    *H01L 41/113*     (2006.01)
    *H01L 41/00*     (2013.01)
    *H01L 41/312*     (2013.01)
    *A61N 1/378*     (2006.01)
    *H01L 41/047*     (2006.01)
    *H01L 41/25*     (2013.01)
    *H02N 2/00*     (2006.01)
    *A61N 1/375*     (2006.01)

(52) U.S. Cl.
    CPC .......... *H01L 41/0478* (2013.01); *H01L 41/08* (2013.01); *H01L 41/081* (2013.01); *H01L 41/113* (2013.01); *H01L 41/1134* (2013.01); *H01L 41/25* (2013.01); *H01L 41/312* (2013.01); *H02N 2/22* (2013.01); *A61N 1/3756* (2013.01)

(56) References Cited

U.S. PATENT DOCUMENTS

| | | | | |
|---|---|---|---|---|
| 8,456,063 B2 * | 6/2013 | Jager | ................... | H01L 41/1138 310/339 |
| 8,552,573 B2 * | 10/2013 | Shaban | .................... | H01G 5/01 290/1 E |
| 9,871,472 B2 * | 1/2018 | Jia | ............................. | F03G 7/08 |
| 10,097,112 B2 * | 10/2018 | Nguyen-Dinh | ..... | H01L 41/1138 |
| 10,447,177 B2 * | 10/2019 | Karami | ................... | H02N 2/18 |
| 10,727,394 B1 * | 7/2020 | Bulsara | ..................... | F03G 7/08 |
| 10,777,730 B2 * | 9/2020 | Behera | ..................... | H02N 2/02 |
| 2003/0227233 A1 | 12/2003 | Maushard et al. | | |
| 2004/0251781 A1 | 12/2004 | Bouche et al. | | |
| 2005/0104478 A1 | 5/2005 | Xu et al. | | |
| 2007/0200459 A1 | 8/2007 | Yoshino et al. | | |
| 2008/0092354 A1 * | 4/2008 | Clingman | ............... | H01L 41/25 29/25.35 |
| 2008/0100180 A1 | 5/2008 | Clingman et al. | | |
| 2008/0136292 A1 * | 6/2008 | Thiesen | ................. | H02N 2/186 29/25.35 |
| 2009/0085442 A1 * | 4/2009 | Kozinsky | ............... | H02N 2/188 310/339 |
| 2010/0141096 A1 | 6/2010 | Churchill et al. | | |
| 2012/0086310 A1 * | 4/2012 | Allaei | .................... | H02N 2/185 310/339 |
| 2012/0326565 A1 | 12/2012 | Kuisma et al. | | |
| 2013/0193930 A1 | 8/2013 | Baugher | | |
| 2014/0070670 A1 * | 3/2014 | Burgueno | ................ | H02N 2/18 310/339 |
| 2015/0303835 A1 | 10/2015 | Katsumura et al. | | |

FOREIGN PATENT DOCUMENTS

| | | |
|---|---|---|
| JP | 3939737 B1 | 7/2007 |
| JP | 2012156591 A | 6/2012 |

* cited by examiner

PIEZOELECTRIC ENERGY HARVESTING USING A NONLINEAR BUCKLED BEAM AND METHOD FOR SAME

CROSS-REFERENCE TO RELATED APPLICATIONS

This application claims priority to U.S. Provisional Application No. 62/377,221, filed on Aug. 19, 2016, the disclosure of which is incorporated herein by reference.

FIELD OF THE DISCLOSURE

The present disclosure relates to energy harvesters, and more specifically, piezoelectric energy harvesters.

BACKGROUND OF THE DISCLOSURE

Modern cardiac pacemakers require batteries and, therefore, necessitate repeated surgical replacements over the life of the patient who needs heart rate support. Usage of batteries is more challenging in leadless pacemakers compared to conventional pacemakers. The miniature size of leadless pacemaker necessitates minuscule batteries and up until recently, no battery technology could reliably power leadless pacemakers. Still, the current leadless pacemaker batteries are depleted in less than twelve years. This demands placement of another leadless pacemaker in the heart.

By contrast, energy harvesters generate power continuously and never run out of power. However, high natural frequency is a common problem in microelectromechanical systems ("MEMS") energy harvesters. Different methods have been used to decrease the natural frequencies of the energy harvesters in order to increase the output power of the device.

BRIEF SUMMARY OF THE DISCLOSURE

The present disclosure provides a piezoelectric energy harvester (EH), which converts motions, such as, for example, biological motions including myocardial motion, Jung motion, diaphragm motion, blood flow in the blood vessels, etc. into electricity. In one embodiment, the energy harvester is optimized for the harvesting of myocardial or cardiac motion. The generated power can be used to power biomedical sensors and devices inside the body. In one embodiment, the power can be used to power leadless pacemakers. Modeling showed that our EH can generate enough power to power a leadless pacemaker using heartbeat vibrations. Modeling also showed that the device is robust to the change in the heart rates and generates sufficient power for powering a pacemaker over a wide range. The modeling results show that exemplary heart motion energy harvesters of the present disclosure generate more power than the same size batteries in a leadless pacemaker.

Some embodiments of the present energy harvester comprise a nonlinear, thermally buckled bimorph piezoelectric beam confined in a rigid frame. In some embodiments, the system is assembled at high temperature and operated at the body temperature. The difference in the thermal coefficients of expansion of the beam and the frame cause the beam to buckle at operating temperature (e.g., body temperature). This intentional buckling makes the beam unstable and nonlinear, which improves the power production and robustness of the device. A typical energy harvester having a size compatible with leadless pacemakers, e.g., 0.5 cm$^3$, would be expected to have a high natural frequency. In embodiments of the present design, the natural frequency can be lowered significantly by using a buckled beam. A mass is placed approximately at the middle of the beam to decrease the natural frequency even more. The natural frequencies and mode shapes of the EH were analytically derived and are shown herein. The terms corresponding to geometric nonlinearities are included in the electromechanical coupled governing equations.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 21A:
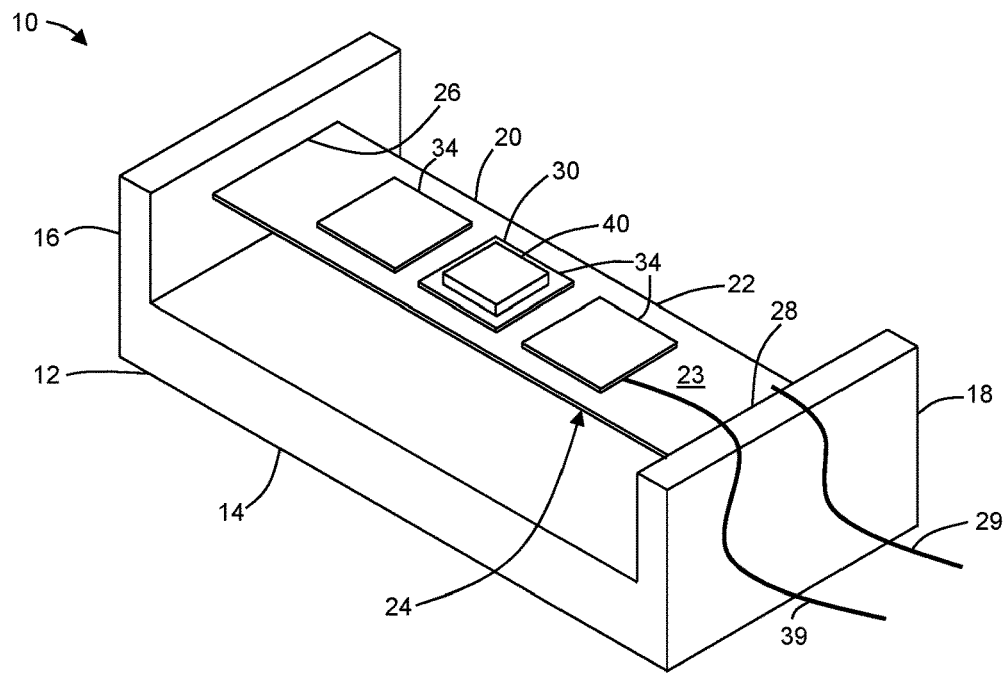
FIG. 21A is a perspective view of an energy harvester according to another embodiment of the present disclosure.
Figure 21B:
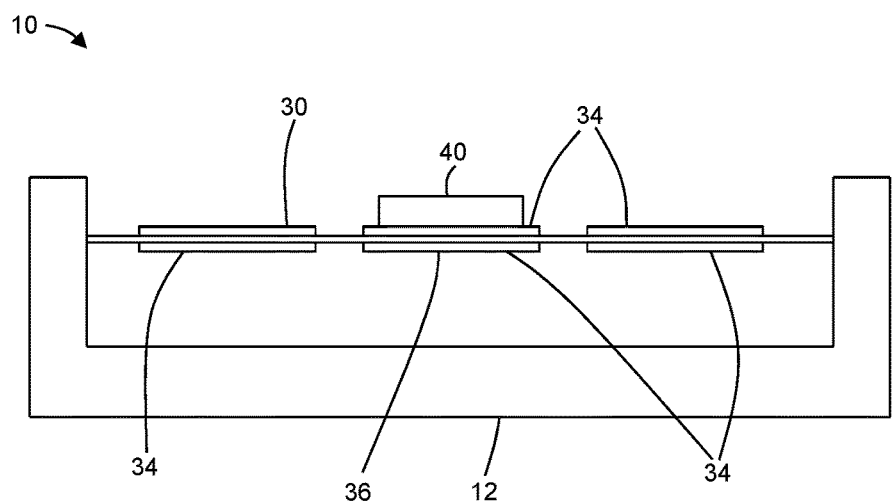
FIG. 21B is a side elevation view of the energy harvester of FIG. 21A.

With reference to FIGS. 21A and 21B, the present disclosure may be embodied as an energy harvester 10 for harvesting energy from an external force, such as, for example, an external vibratory force. The energy harvester 10 comprises a frame 12 having a base 14, a first side member 16 affixed to the base 14, and a second side member 18 affixed to the base 14 and spaced apart from the first side member 16. A first buckled beam 20 is coupled between the first side member 16 of the frame 12 and the second side member 18 of the frame 12.

The first buckled beam 20 has a substrate layer 22 which is elastically deformable in response to a force, such as, for example, a vibratory force. The substrate layer 22 has a first face 23 and a second face 24, which is opposite to the first face 23. The substrate layer 22 extends from a first end 26 to a second end 28. The first end 26 is affixed to the first side member 16 of the frame 12 and the second end 28 is affixed to the second side member 18 of the frame 12. The substrate layer 22 includes a terminal 29 for electrical connection to a load.

The first buckled beam 20 has a first piezoelectric layer 30 joined to the first face 23 of the substrate layer 22. The first piezoelectric layer 30 has a terminal 32 for electrical connection to a load. In this way, a load may be connected (directly or indirectly) across terminal 29 of the substrate layer 22 and terminal 32 of the first piezoelectric layer. The first piezoelectric layer 30 includes at least one piezoelectric patch 34 (e.g., a patch of piezoelectric material which can accumulate an electric charge in response to applied mechanical stress). In some embodiments, the first piezoelectric layer 30 comprises two or more piezoelectric patches 34, for example, the first piezoelectric layer may comprise four piezoelectric patches.

The first buckled beam 20 may further include a second piezoelectric layer 36 joined to the second face 24 of the substrate layer 22. The second piezoelectric layer 36 has a terminal 32 for electrical connection to the first piezoelectric layer 30. In some embodiments, the first and second piezoelectric layers 30, 36 are electrically connected in parallel. In other embodiments, the piezoelectric layers may be connected to each other in series. The second piezoelectric layer 36 includes at least one piezoelectric patch 34. In some embodiments, the second piezoelectric layer 30 comprises two or more piezoelectric patches 34, for example, the second piezoelectric layer may comprise four piezoelectric patches. The second piezoelectric layer 36 may have the same number of piezoelectric patches as the first piezoelectric layer or the layers may have a different number of piezoelectric patches from each other.

The first buckled beam 20 may further comprise a mass 40 connected to the substrate layer 20. It is known that a beam, such as the first buckled beam 20 will have a natural frequency. By connecting a mass 40 to the first buckled beam 20, the natural frequency of the beam can be changed (as further described below). The mass 40 can be directly connected to the substrate layer 22 or indirectly, such as, for example, by connection to the first or second piezoelectric layers. In some embodiments, the mass 40 is connected to the substrate layer 22 at a location equidistant from the first end 26 and the second end 28. In some embodiments, the mass 40 is made up of more than one component.

In some embodiments, the frame 12 is made from a material having a coefficient of thermal expansion (CTE) which differs from the CTE of a material of the first buckled beam 20. For example, the frame 12 may be made from cast iron, and the beam 20 may be made from brass. In some embodiment, the CTE of the frame 12 is greater than the CTE of the first beam 20. In this way, the energy harvester 10 may be made with a buckled (elastically deformed) beam by assembling the energy harvester at an assembly temperature that is higher than an operating temperature (as further described below). In a particular embodiment, the CTE of the frame differs from the CTE of the first beam according to $$T_{diff} = \frac{\Delta}{L(\alpha_f - \alpha_{eq})},$$

where $T_{diff}$ is a temperature difference, $\Delta$ is an axial displacement of the first beam due to thermal compression of the frame, L is a length of the first beam, $\alpha_f$ is the CTE of the frame, and $\alpha_{eq}$ is the CTE of the first beam.

Figure 22:
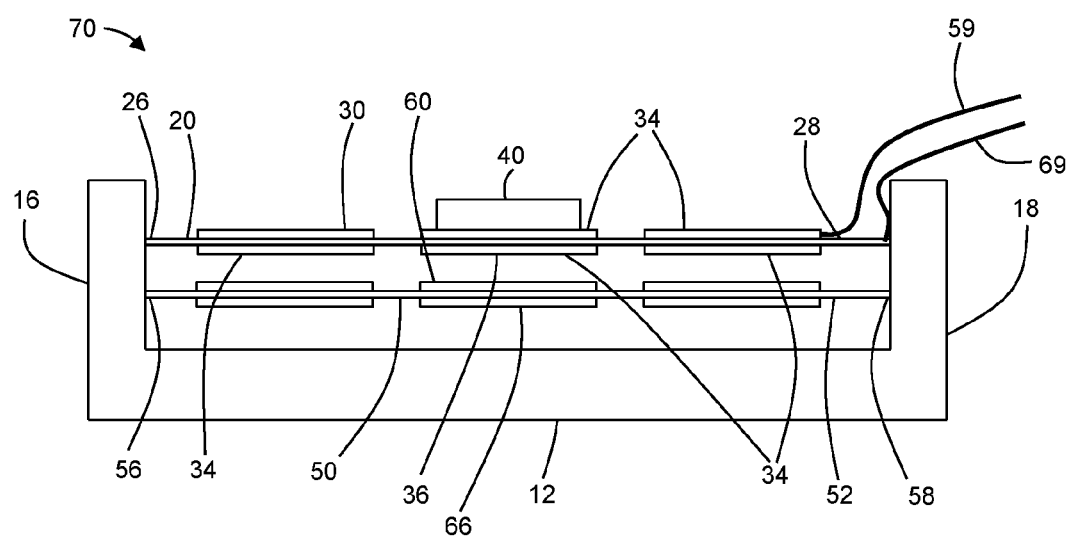
FIG. 22 is a perspective view of an energy harvester according to another embodiment of the present disclosure.

In some embodiments, an energy harvester 70 may further comprise a second buckled beam 50 coupled between the first side member 16 of the frame 12 and the second side member 18 of the frame 12 (see, for example, FIG. 22). The second buckled beam 50 may be configured as described above with respect to the first buckled beam 50. For example, the second buckled beam 50 has a substrate layer 52 with a first end 56 affixed to the first side member 16 of the frame 12, and a second end 58 affixed to the second side member 58 of the frame 12. The second buckled beam 50 has a first face 53, a second face 54 opposite to the first face 53, and a terminal 59 for electrical connection to a load. The substrate layer 52 is elastically deformable in response to the external force. The second buckled beam 50 further comprises a first piezoelectric layer 60 joined to the first face 53 of the substrate layer 52 and having a terminal 69 for electrical connection to a load. The first piezoelectric layer 60 of the second buckled beam 50 comprises at least one piezoelectric patch 64. The second buckled beam 50 may have a second piezoelectric layer 66. The first buckled beam 20 and the second buckled beam 60 of an energy harvester 10 may or may not be configured the same as one another.

Figure 23:
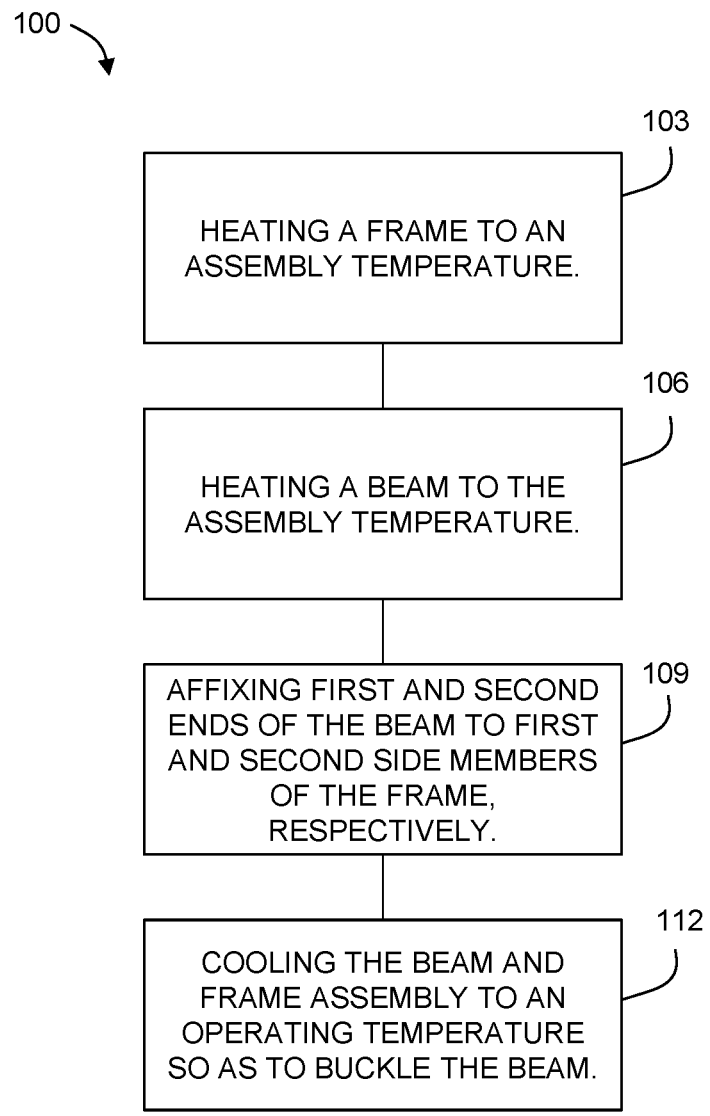
FIG. 23 is a chart showing a method according to another embodiment of the present disclosure.

With reference to FIG. 23, the present disclosure may be embodied as a method 100 of making a buckled-beam energy harvester for harvesting energy at an operating temperature. For example, the energy harvester may be similar to those described above. The method 100 includes heating 103 a frame to an assembly temperature. The frame has a first side member and a second side member spaced apart from the first side member. The assembly temperature is higher than the operating temperature. The method 100 further includes heating 106 a beam to the assembly temperature. The beam has a first end, a second end, and a coefficient of thermal expansion (CTE) which is less than a CTE of the frame. The beam may comprise a substrate layer joined to a first piezoelectric layer.

The first end of the beam is affixed 109 to the first side member of the frame and the second end of the beam is affixed 109 to a second side member of the frame to form an energy harvester assembly. The energy harvester assembly is cooled 112 to the operating temperature, thereby causing the beam to buckle.

In an embodiment, the disclosed energy harvester comprises:
a) a substrate electrically connected to a load resistor;
b) at least one piezoelectric patch affixed to a top face of the substrate and electrically connected to the load resistor;
c) at least one piezoelectric patch affixed to a bottom face of the substrate, wherein a terminal piezoelectric patch affixed to the top face of the substrate is electrically connected to a terminal piezoelectric patch affixed to the bottom face of the substrate;
d) a frame to which the substrate is clamped on both ends, wherein the difference between a thermal coefficient of the frame and a thermal coefficient of the substrate satisfies the equation, $$T_{diff} = \frac{\Delta}{L(\alpha_f - \alpha_{eq})};$$

and
e) a mass affixed to the at least one piezoelectric patch on the top face of the piezoelectric patch substantially at a center of the substrate.

In an embodiment, the electrical connection of (c) is a parallel connection. However, if desired, a series connection may be used.

When the at least one piezoelectric patch on the top face or on the bottom face of the substrate comprises more than one piezoelectric patch, said patches on each face are connected to each other in parallel in an embodiment. However, if desired, a series connection may be used.

The piezoelectric patches may be affixed to the substrate by a conductive means, such as a conductive epoxy.

The at least one piezoelectric patch affixed to the top face of the substrate and the at least one piezoelectric patch affixed to the bottom face of the substrate may each independently be any number of patches. In an embodiment, the at least one piezoelectric patch on the top face of the substrate consists of four piezoelectric patches and the at least one piezoelectric patch on the bottom face of the substrate consists of four piezoelectric patches. In another embodiment, the at least one piezoelectric patch on the top face of the substrate consists of two piezoelectric patches and the at least one piezoelectric patch on the bottom face of the substrate consists of two piezoelectric patches. In another embodiment, the at least one piezoelectric patch on the top face of the substrate consists of six piezoelectric patches and the at least one piezoelectric patch on the bottom face of the substrate consists of six piezoelectric patches.

In an embodiment, the substrate is made of brass due to its high density and high module of elasticity.

In an embodiment, the substrate has a length of about 1 cm to about 2 cm, a width of about 1.25 cm to about 1 cm and a thickness of about 0.005 cm to about 0.02 cm. In one embodiment, the substrate has a length of about 2 cm and a width of about 0.5 cm.

In an embodiment, the piezoelectric patches each have a thickness ($t_p$) of about 0.005 cm to about 0.02 cm.

In an embodiment, the frame is made from cast iron.

In one embodiment, the frame contains at least one aperture.

Figure 12A:
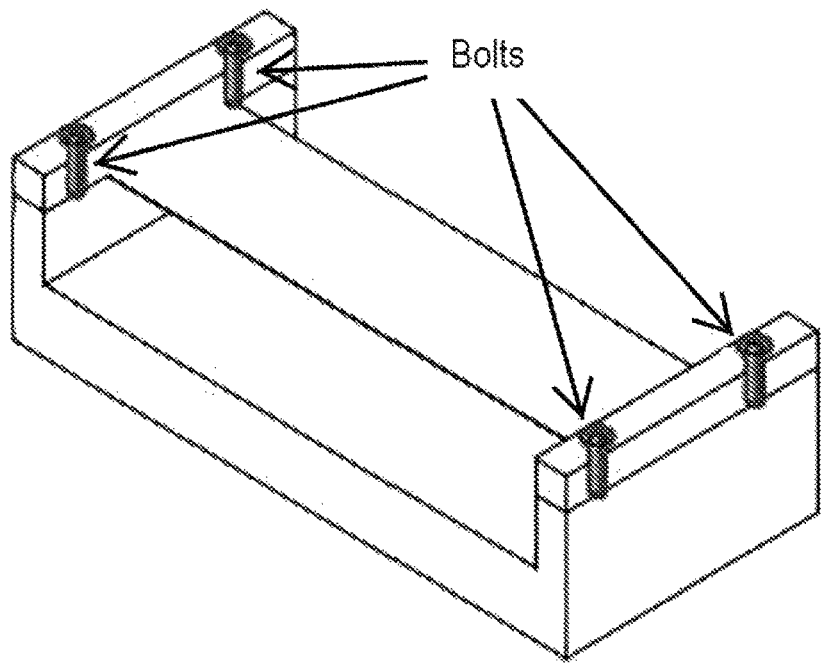
FIG. 12A is a perspective view of an energy harvester according to an embodiment of the present disclosure.
Figure 12B:
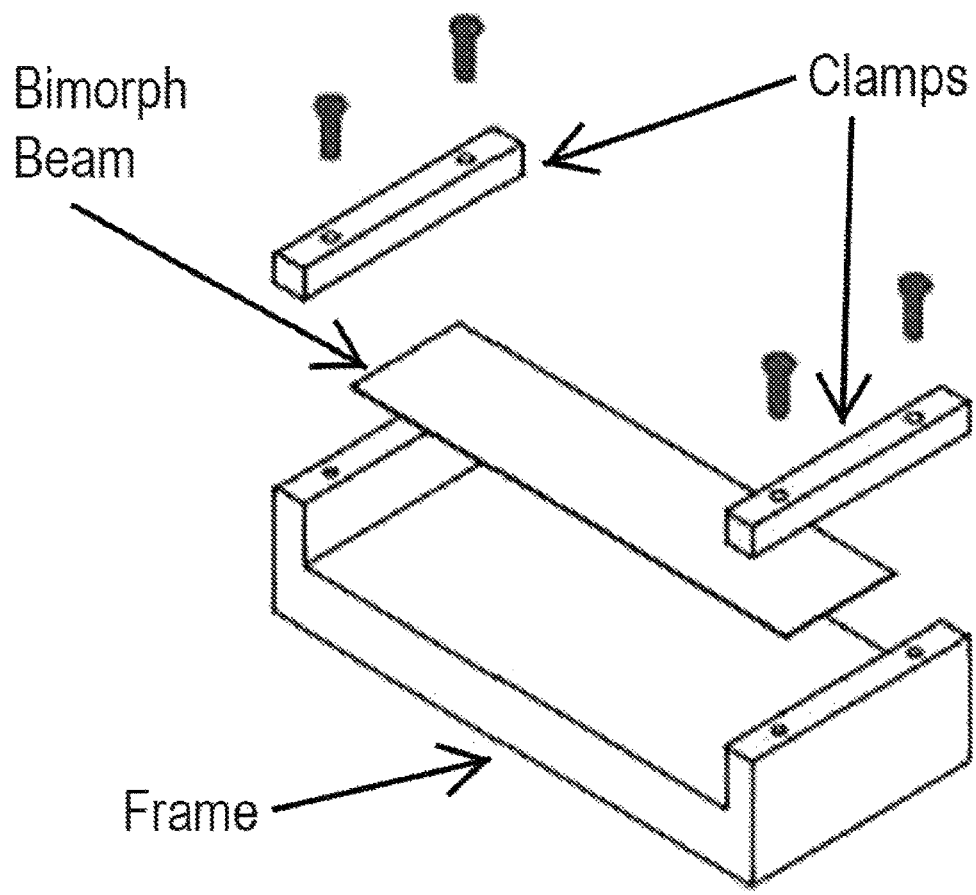
FIG. 12B is an exploded view diagram of the energy harvester of FIG. 12A.
Figure 13:
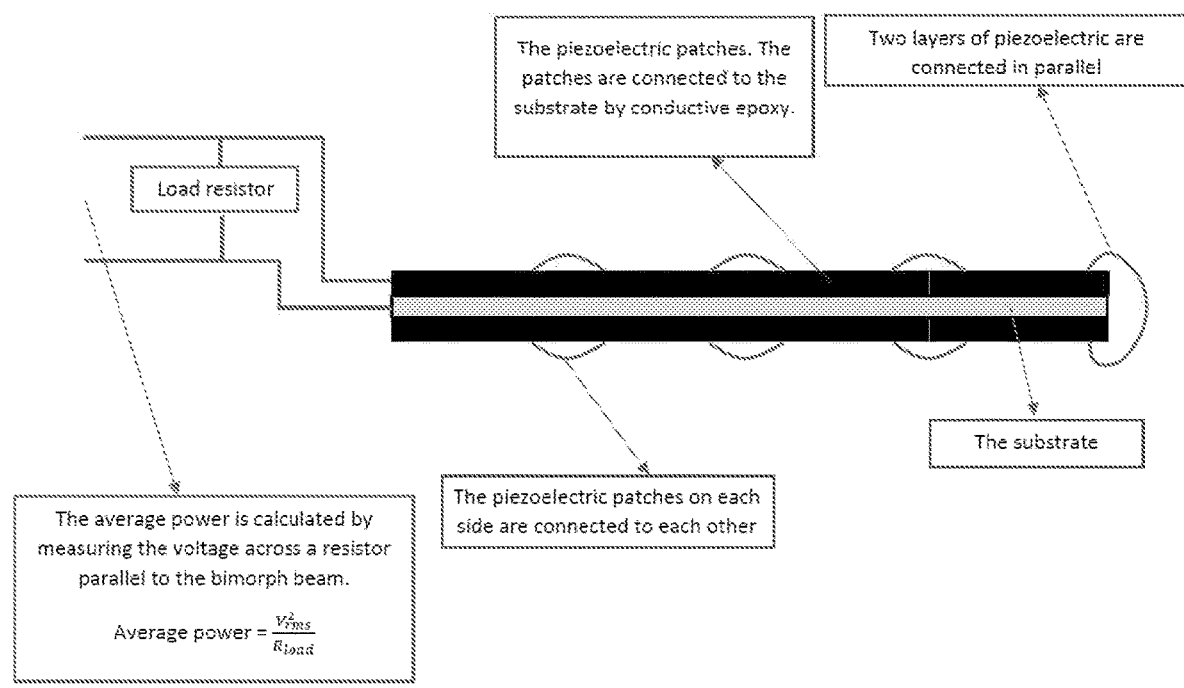
FIG. 13 is a diagram of a buckled beam (bimorph beam) according to the present disclosure having two piezoelectric layers connected in parallel
Figure 14:
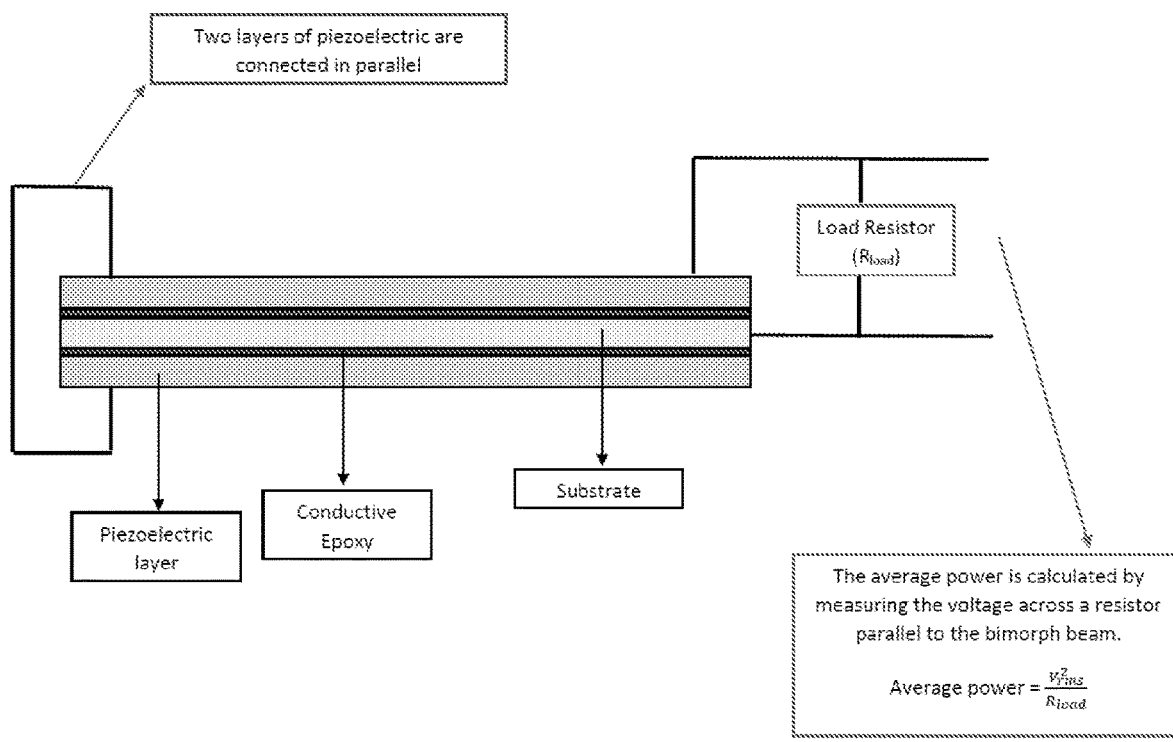
FIG. 14 is a diagram of a buckled beam (bimorph beam) according to the present disclosure having two piezoelectric layers connected in parallel.

In one embodiment, the clamping on each end of the substrate is performed by a clamp and at least one bolt as illustrated in FIGS. 12A and 12B. In this embodiment, the clamp contains a least one aperture through which the bolt is inserted into a corresponding aperture on the frame. The dual clamping creates a clamped boundary condition for the design and is also known as clamped-clamped. The bolts may be off the shelf steel bolts.

In an embodiment, the clamp is made from cast iron.

In an embodiment, the clamp is made from the same material as the frame.

In an embodiment, the mass is made from platinum or tungsten due to the high densities of those materials.

In an embodiment, the mass has a density of more than 18 g/cm$^3$.

In an embodiment, the mass has a weight of 5 g to 20 g. In one embodiment, the weight of the mass is 10 g.

The mass may be affixed to the at least one piezoelectric patch by, e.g., an epoxy.

This epoxy may be conductive or may not be conductive.

In an embodiment, the energy harvester has a volume of about 0.5 cm$^3$ to about 1.0 cm$^3$.

In an embodiment, the substrate is made from brass having a thickness of about 0.01 cm. In an embodiment, the piezoelectric patches on the top and bottom faces of the substrate are lead zirconate titanate (PZT). In a more preferred embodiment, the lead zirconate titanate is DOD Type VI, Navy Type VI, Industry Type 5H, such as PSI-5H4E piezoceramic available form Piezo Systems, Inc., Woburn, Mass. (see http://piezo.com/prodmaterialprop.html and http://piezo.com/prodmaterial0nav.html). In an embodiment, the piezoelectric patches each have a thickness ($t_p$) of about 0.01 cm. In an embodiment, the substrate has a length of about 2 cm and a width of about 0.25 cm. In an embodiment, the mass consists of platinum and has a weight of 5 g. As used herein, "The Specimen" refers to the specimen having all of the preferred and the more preferred embodiments set forth in this paragraph.

As used herein, the "bimorph beam" comprises:
(a) a substrate;
(b) at least one piezoelectric patch affixed to the top face of the substrate;
(c) at least one piezoelectric patch affixed to the bottom face of the substrate, wherein a terminal piezoelectric patch affixed to the top face of the substrate is electrically connected to a terminal piezoelectric patch affixed to the bottom face of the substrate.

The "bimorph beam" is used at times to reference the two layers of piezoelectric patches (one layer on each of the top and the bottom faces of the substrate). Each layer comprises at least one piezoelectric patch.

As used herein, "a" and "the" encompass the singular and plural forms.

Optionally, a back-up battery may be electrically connected to the energy harvester.

The coupled governing equation of a buckled piezoelectric beam is written as:

$$m\frac{\partial^2 w_{rel}}{\partial t^2} + c\frac{\partial w_{rel}}{\partial t} + \tag{1}$$

$$EI\frac{\partial^4 w_{rel}}{\partial x^4} + \left[P_c + K_{eq}\Delta - \frac{K_{eq}}{2}\int_0^L \left(\frac{\partial w_{rel}}{\partial x}\right)^2 dx\right]\frac{\partial^2 w_{rel}}{\partial x^2} =$$

Figure 1:
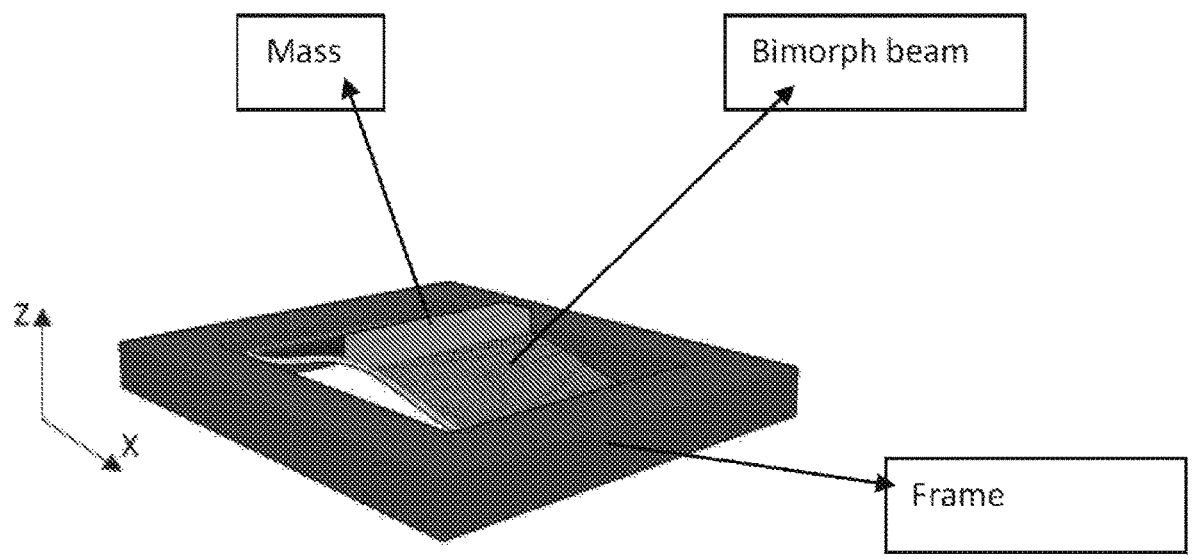
FIG. 1 is a schematic view of a thermally buckled beam clamped at both ends in a rigid frame.
Figure 2:
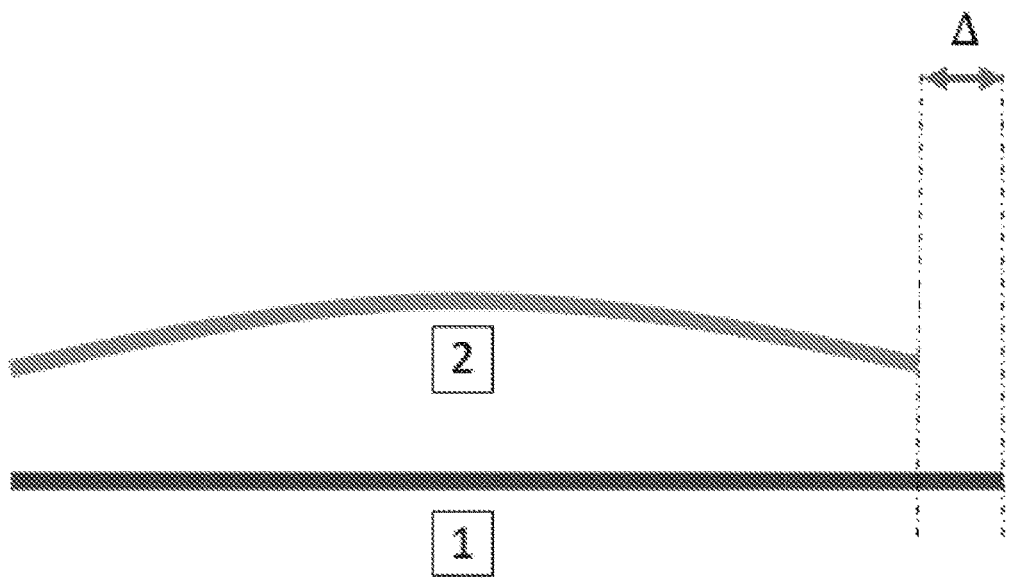
FIG. 2 is a diagram showing axial shortening of the beam ($\Delta$) where (1) depicts an unbuckled beam and (2) depicts a buckled beam.
Figure 3:
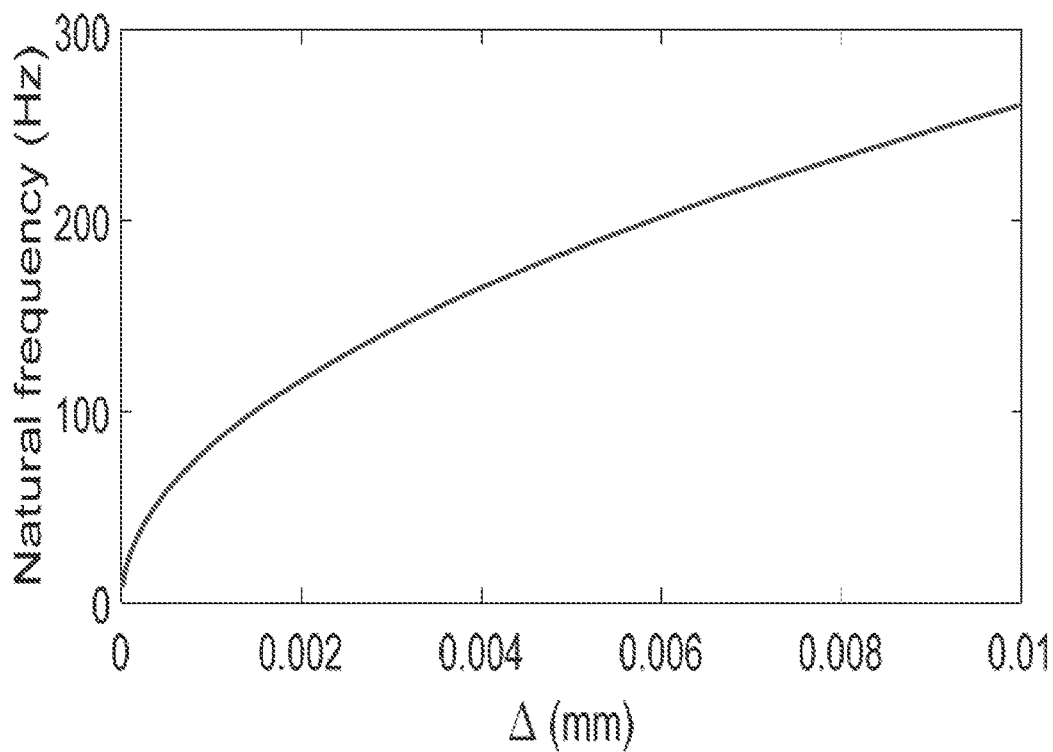
FIG. 3 is a graph showing the effect of shortening of the beam on its natural frequency.

-continued $$-2\alpha\left[\left(\frac{d\delta(x)}{dx} - \frac{d\delta\left(x - \frac{L}{4}\right)}{dx}\right) + \left(\frac{d\delta\left(x - \frac{L}{2}\right)}{dx} - \frac{d\delta\left(x - \frac{L}{4}\right)}{dx}\right)\right]$$

$$v(t) - [m + M_{mid}\delta(x - x_{mid})]\frac{d^2w_b}{dt^2}$$

where m is the total mass per unit length of the beam, $w_{rel}(x,t)$ is deflection along the z-axis, c is the damping term, EI is the equivalent bending stiffness of the beam, $P_c$ is the first critical buckling force, Δ is the axial displacement due to the thermal compressing (FIG. 2), $K_{eq}$ is the equivalent axial stiffness of the beam, a is the piezoelectric coupling coefficient, and V is the voltage across the piezoelectric elements which are connected in parallel. δ(x) is Dirac delta function. In the above equation, $M_{mid}$ represents the middle mass and $w_b$ is the base displacement. Using modal analysis, the continuous differential equations can be discretized as:

$$\begin{cases} \ddot{T} + c\dot{T} + (K+p)T + NT^3 + \chi V(t) = \gamma \ddot{w}_b \\ C_p\dot{V} + \frac{V}{R_1} = -\chi\dot{T} \end{cases} \quad (2)$$

where T is the temporal term, c is the damping ratio, K stands for the linear stiffness, the reduction of the stiffness coefficient due to the axial force is p, N is the nonlinear coefficient, the coupling coefficient is x, $R_1$ is the shunt resistor and $C_p$ is the internal capacitance for the piezoelectric layer. The new natural frequency of the beam after being buckled is calculated as:

$$\omega = \sqrt{(K+p) + 3NT_{st}^2} \quad (3)$$

where $T_{st}$ is coordinate of the thermal term for the equilibrium point. FIG. 3 shows the change in the natural frequency of a bimorph beam with the change in the amount of the axial shortening of the beam (Δ). The lower the delta, the lower the natural frequency. Theoretically, we can have zero natural frequency when the delta is zero and the beam is about to buckle (K+p=0).

The dimensions of the piezoelectric EH were optimized through numerical simulations. Different materials with different thicknesses were tested for the various amount of the axial shortening of the beam. In order to prevent charge cancellations, the piezoelectric layer is electrically divided into four segments. A middle mass is used to reduce the natural frequency and increase the generated power. Both ends of the beam are clamped inside the outer frame. For a given beam and a specific compression (Δ) in the beam, we find the first buckled natural frequency and mode shape. Then we solve the governing equations using the heartbeat vibrations as the base acceleration of the EH and calculate the power. The power is calculated by $P_{ave}=$ $$\frac{v_{rms}^2}{R}.$$

Where R is the load resistor parallel to the EH. The piezoelectric patches are connected in parallel. Having them in parallel keeps the voltage constant and adds their charges. The parallel configuration gives us the maximum power in this test. The generated power can be used to power leadless pacemakers or other biomedical devices inside the body. We use the heartbeat acceleration in the time domain measured by Kanai.

Figure 4:
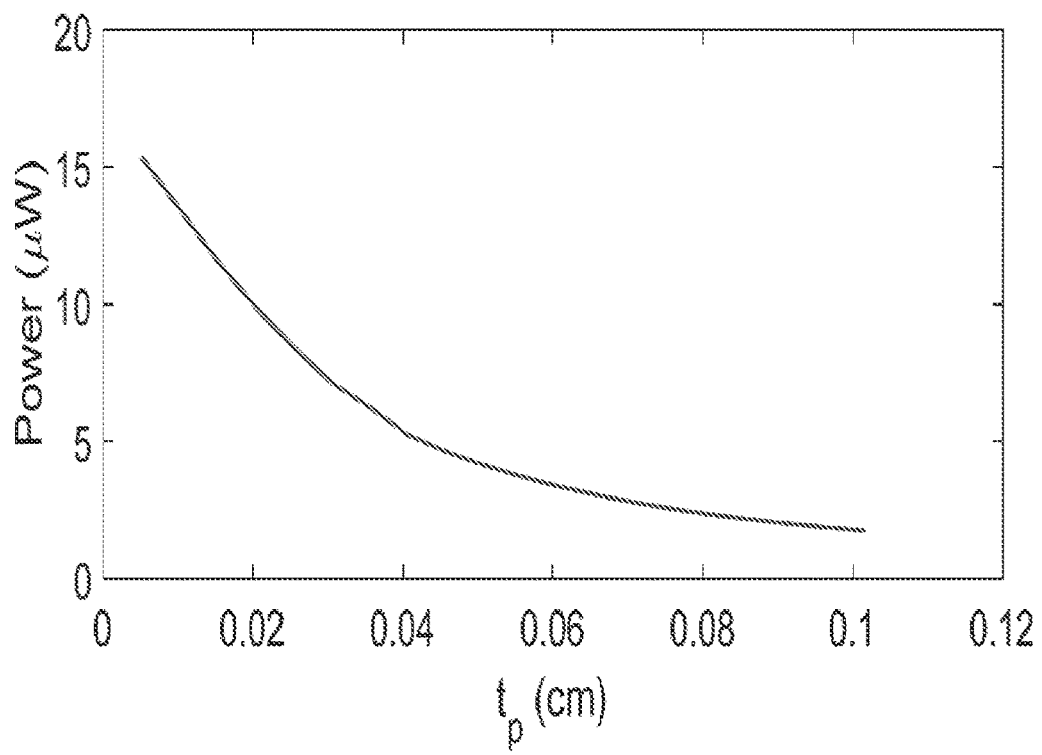
FIG. 4 is a graph showing the effect of thickness of the piezoelectric layer on the average power output. ($\Delta$=0.15 μm, $t_s$=0.01 cm)
Figure 5:
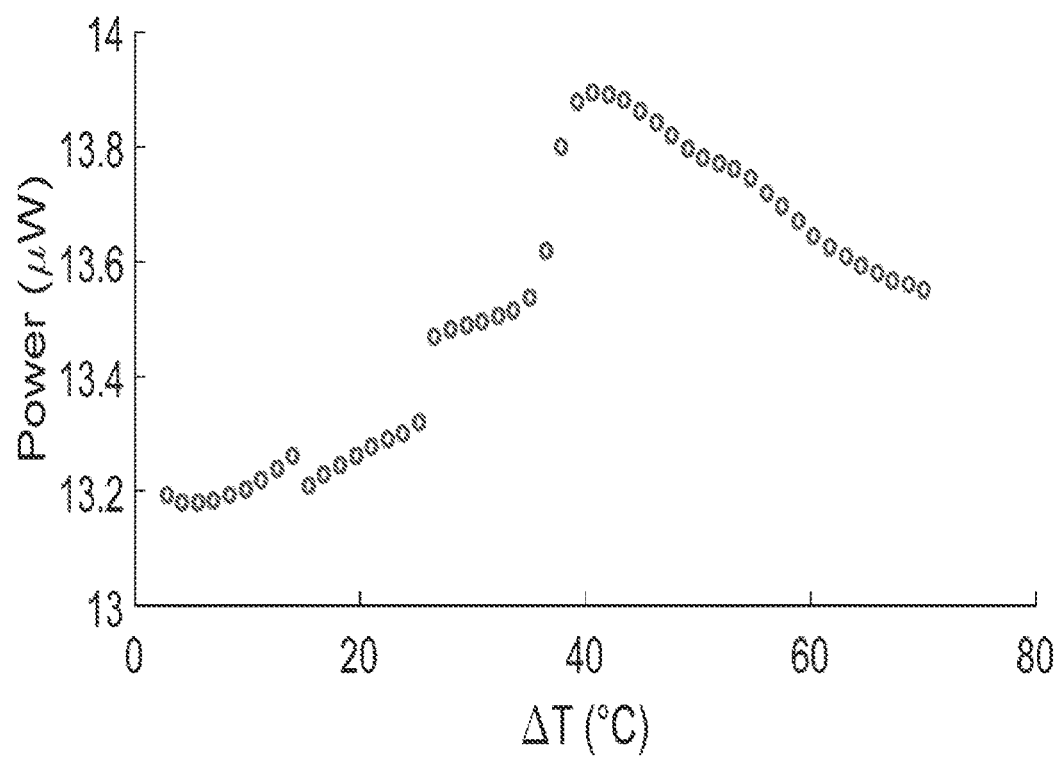
FIG. 5 is a graph showing the effect of the temperature difference of the power output.

FIG. 4 shows the effect of the piezoelectric layer thickness on the average power output of The Specimen with a fixed Δ. The thicker layers generate less amount of power comparing to thin layers. 0.01 cm is currently the thinnest available piezoelectric layer in the market and is chosen as the thickness of the piezoelectric layer. FIG. 5 shows the power output versus the temperature difference. The temperature difference is used to buckle the beam thermally. As can be seen from FIG. 5, a wide range of temperature differences can be used. While it is possible to use a temperature difference of more than 70 degrees, we prefer not to exceed this differential. Cast iron is used as the material for the frame.

Figure 6:
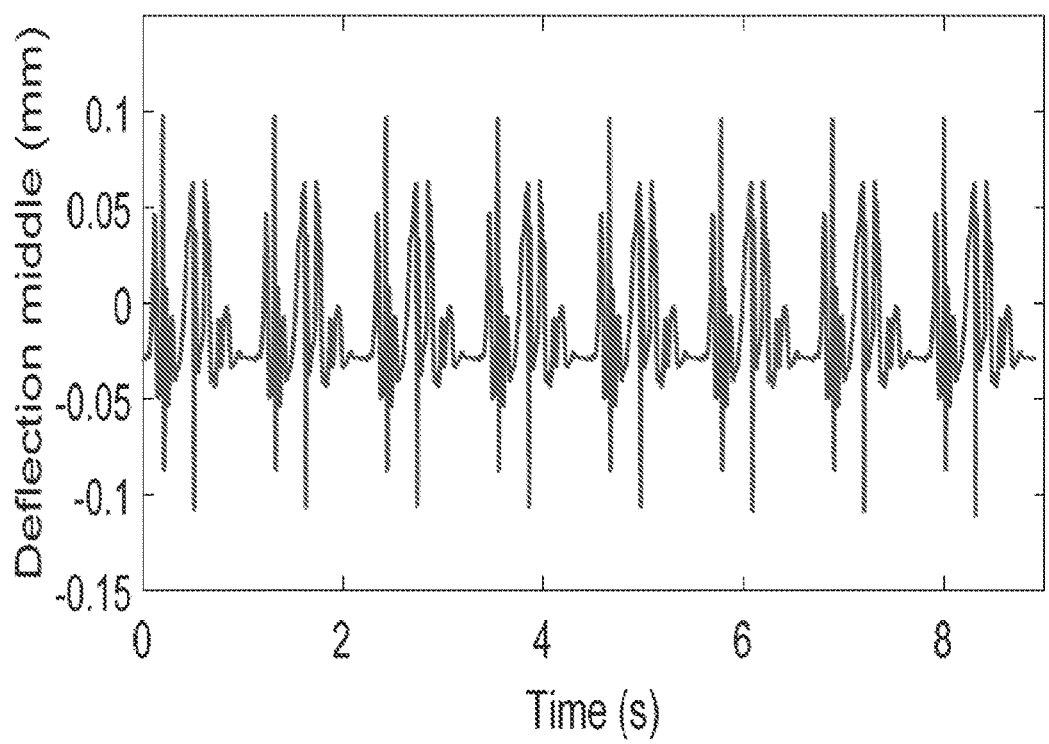
FIG. 6 is a graph showing deflection of the middle of the active beam due to heartbeat acceleration.

For The Specimen, Δ is assumed to be 0.15 μm to maximize the power output. Using the equation (3), we find the first natural frequency as 31.92 Hz. This frequency is much lower than the natural frequency of the unbuckled beam (210.68 Hz). We consider two safety factors for our device. One is the axial safety factor which corresponds to the axial stress in the beam. The other one is the safety factor due to bending deformation of the beam. Each of these safety factors is calculated for the substrate and the piezoelectric layer to avoid any damages to the beam. After solving the equations, the temporal term of the deflection and the voltage across the resistor are calculated. FIG. 6 shows the deflection of the middle part of the beam due to the heartbeat vibrations. As it is shown in FIG. 6, the beam vibrates around the buckled equilibrium point.

Figure 7:
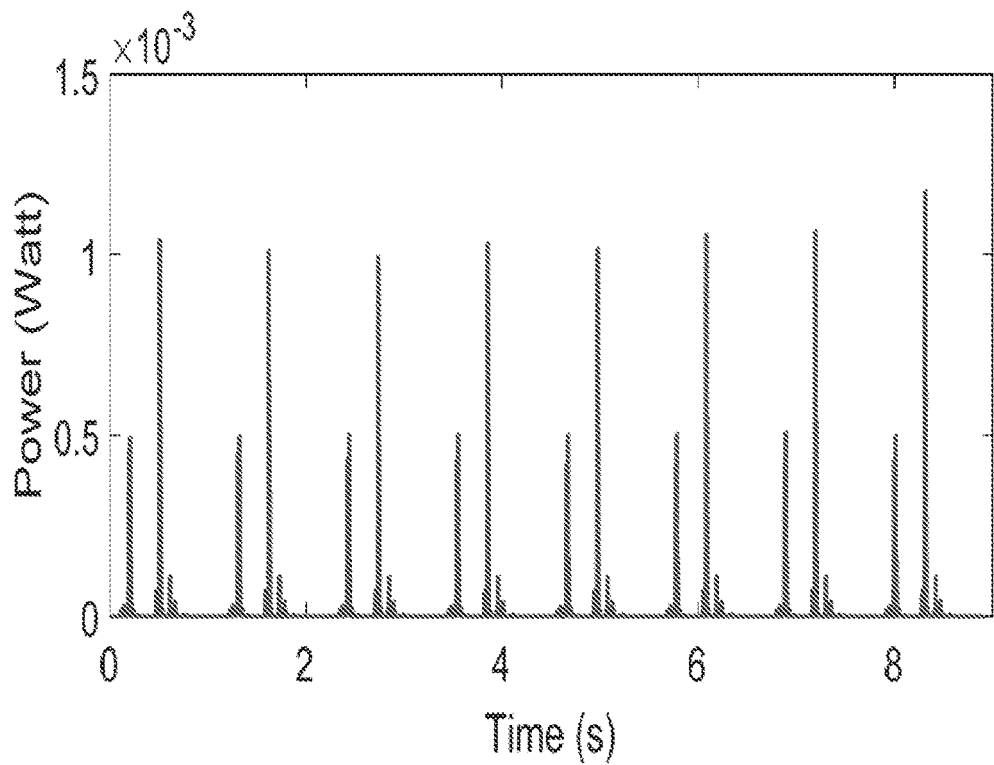
FIG. 7 is a graph showing instantaneous power of the EH from heartbeat vibrations.

FIG. 7 illustrates the instantaneous output power of the energy harvester in the time domain. The average power of the system is calculated as 13.89 μW which is sufficient to power a leadless pacemaker. A leadless pacemaker needs about 10 μW to operate. The shunt resistor is 96 kΩ which is calculated as:

$$R = \frac{1}{C_p\omega} \quad (4)$$

where $C_p$ is the capacitor of the two piezoelectric layers and co is the natural frequency of the EH. For our EH, the internal capacitance for the two piezoelectric layers is 7.83 nF.

Figure 8:
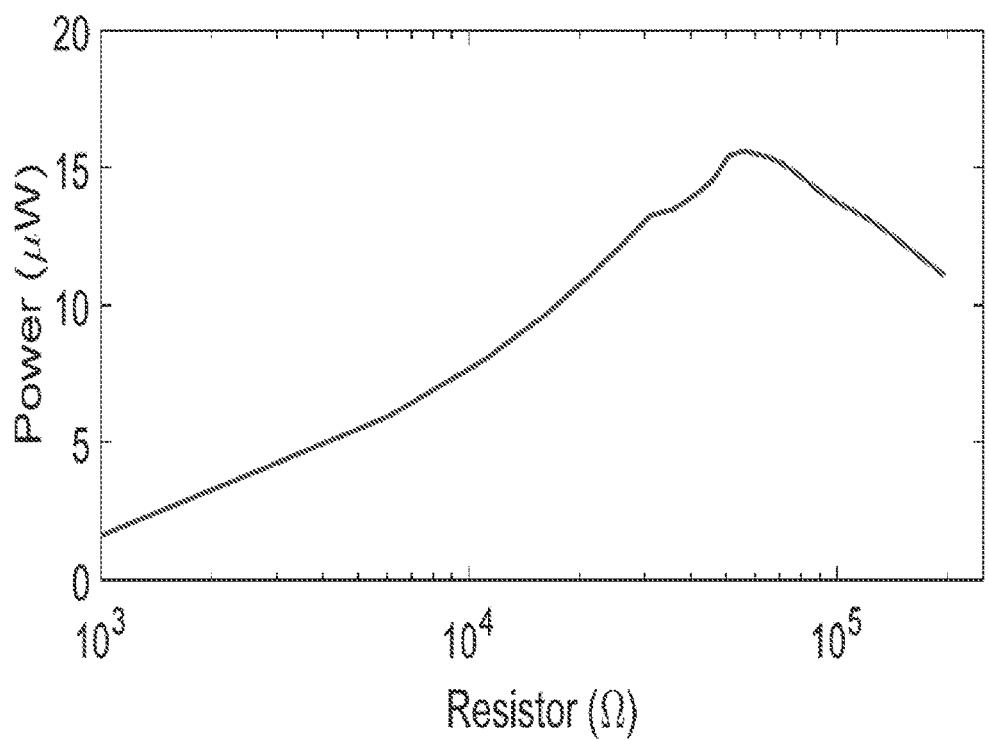
FIG. 8 is a graph showing the effect of the shunt resistor on the output power of the EH.

To find the maximum power, we do a resistor sweep test. FIG. 8 illustrates the effect of the shunt resistor on the output power. The maximum power is 15.61 μW and as predicted the maximum power happens in the vicinity of the resistor calculated from equation (4).

Figure 9:
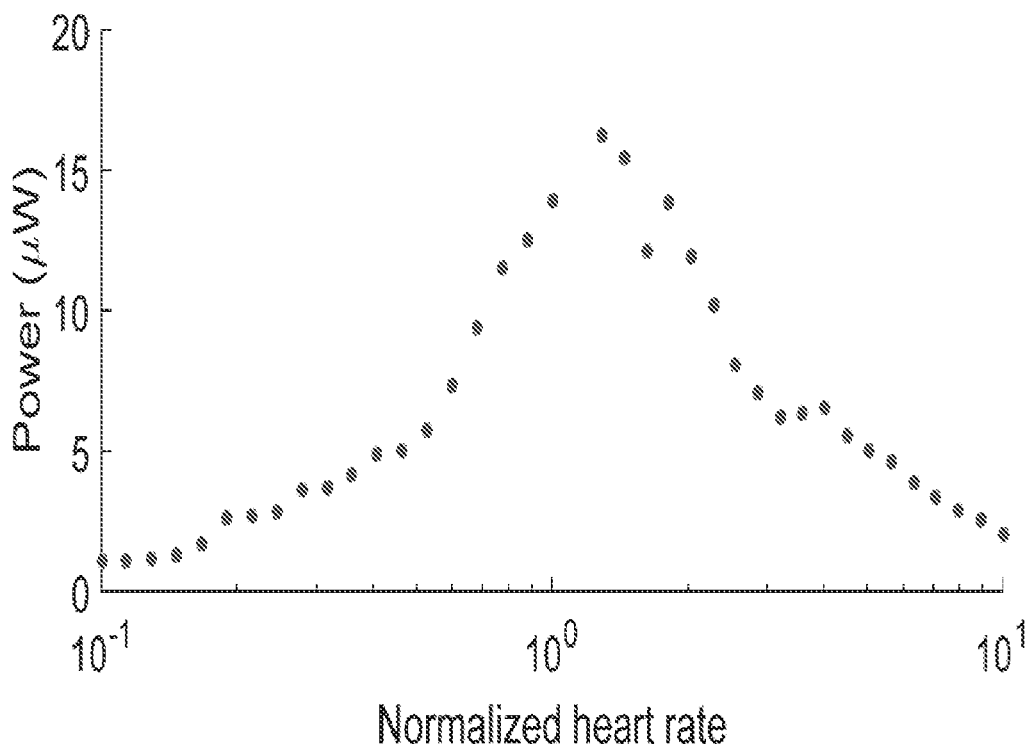
FIG. 9 is a graph showing the output power of the EH for different heart rates.

FIG. 9 shows the effect of the heart rate on the output power. Since the device is nonlinear, it is robust to the heart rate changes. For a wide range (40-195 bpm), the generated power is sufficient for powering a pacemaker (10 μW).

Figure 10:
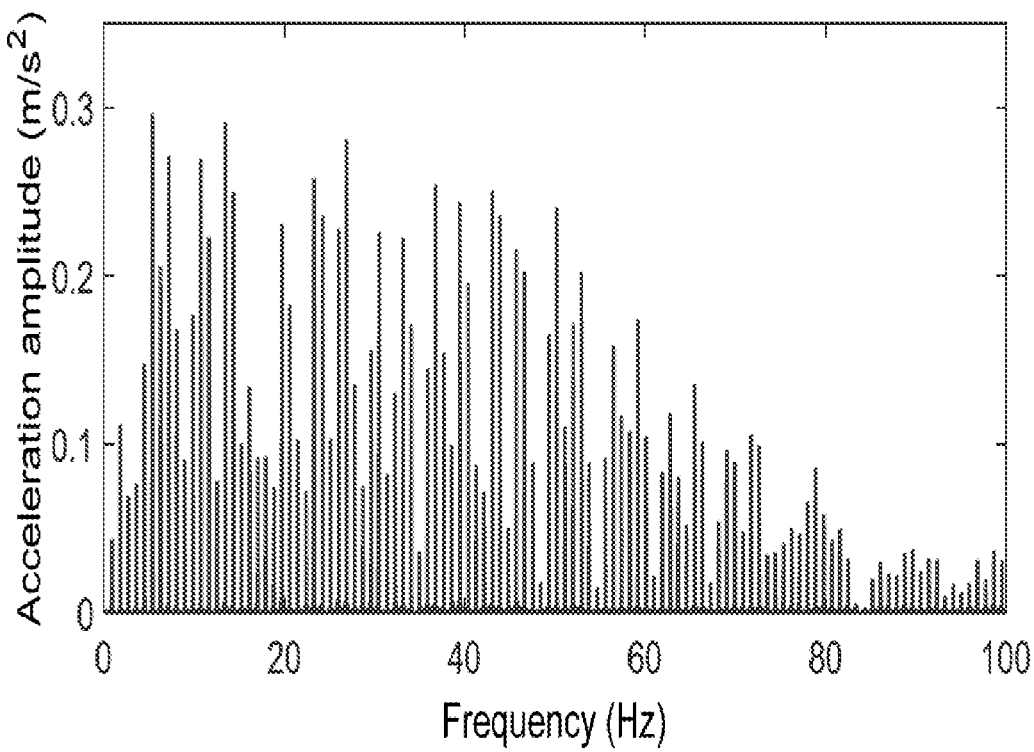
FIG. 10 is a graph showing a Fourier transform of a heartbeat.
Figure 11:
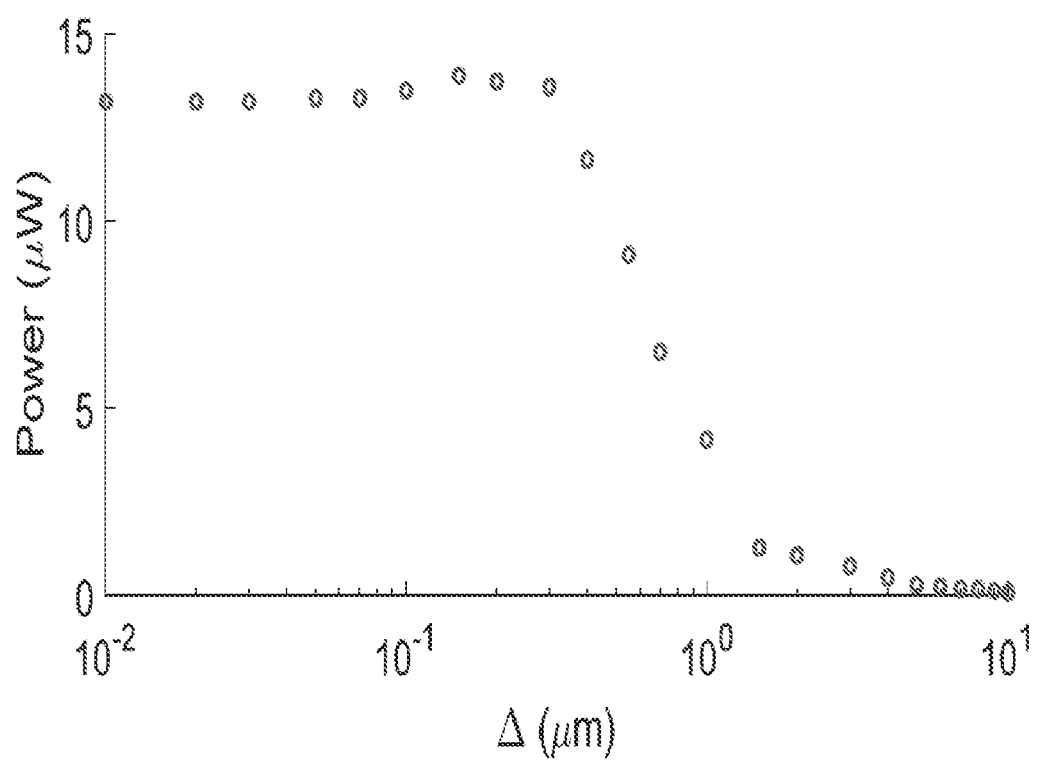
FIG. 11 is a graph showing the effect of the shortening of a beam on the power output.

The inventive energy harvester benefits from a nonlinear design. The beam is thermally buckled and the natural frequency of the beam is reduced. As FIG. 10 shows, the heartbeat vibrations consist of a range of frequencies and most of the high amplitude frequencies are less than 50 Hz. Thus, by lowering the natural frequency, the amount of the average power output of the EH increases. As above (equation 3), the natural frequency of the beam is a function of the amount of the shortening of the beam. In an embodiment, the natural frequency is decreased to less than 35 Hz. FIG. 11 illustrates the effect of the shortening of the beam on the average power output of the EH with the heartbeat vibrations.

FIG. 12 shows an exemplary configuration that can accurately provide a specific amount of A for the beam. The active bimorph beam is clamped inside a frame at a temperature (the assembly temperature) which is sufficiently high to cause the beam to buckle at the designed operating temperature. All the components of the EH including the frame and the bimorph beam will be warmed up to the assembly temperature, and the bimorph beam will be affixed to the frame while at the assembly temperature—a first end of the bean is affixed to a first side member of the frame and a second end of the beam is affixed to a second side member of the frame. In this way, the first and second ends provide the clamped boundary condition on the bimorph beam. After the device cools down, there will be a mismatch between the shortening of the beam and the shortening of the frame. When the frame has a higher Coefficient of Thermal Expansion (CTE) than the CTE of the bimorph beam, the beam will be buckled. For a given Δ, the amount of the temperature difference is calculated as:

$$T_{diff} = \frac{\Delta}{L(\alpha_f - \alpha_{eq})} \quad (5)$$

where L is the length of the beam, $\alpha_f$ is the CTE of the frame, and $\alpha_{eq}$ is the equivalent CTE of the bimorph beam. The equivalent CTE of the bimorph beam is:

$$\alpha_f = \frac{2\alpha_p E_p A_p + \alpha_s E_s A_s}{2 E_p A_p + E_s A_s} \quad (6)$$

where $\alpha_p$, $\alpha_s$ are the CTE of the piezoelectric layer and the substrate, $E_p$, $E_s$ are the module of elasticity of the piezoelectric and the substrate, and $A_p$, $A_s$ are the cross section of the piezoelectric layer and the substrate.

The present disclosure is further described with respect to a model, governing equations, and exemplary embodiments, which are intended to be illustrative and non-limiting.

Modeling and Governing Equations

The governing equation of the beam when it is buckled can be written as:

$$m\frac{\partial^2 w_{rel}}{\partial t^2} + c\frac{\partial w_{rel}}{\partial t} + EI\frac{\partial^4 w_{rel}}{\partial x^4} + \left[P_c + K_{eq}\Delta - \frac{K_{eq}}{2}\int_0^L \left(\frac{\partial w_{rel}}{\partial x}\right)^2 dx\right]\frac{\partial^2 w_{rel}}{\partial x^2} = -2\alpha\left[\left(\frac{d\delta(x)}{dx} - \frac{d\delta(x-\frac{L}{4})}{dx}\right) + \left(\frac{d\delta(x-\frac{L}{2})}{dx} - \frac{d\delta(x-\frac{L}{4})}{dx}\right)\right] v(t) - [m + M_{mid}\delta(x - x_{mid})]\frac{d^2 w_b}{dt^2} \quad (7)$$

where m is the total mass per unit length of the beam, $w_{rel}(x,t)$ is deflection along the z-axis, c is the damping term, EI is the equivalent bending stiffness of the composite beam, $P_c$ is the first critical buckling force, Δ is the axial displacement due to the thermal compression, $K_{eq}$ is the equivalent axial stiffness of the beam, a is the piezoelectric coupling coefficient, and V is the voltage across the piezoelectric elements which are connected in parallel. δ(x) is Dirac delta function. In the above equation $M_{mid}$ represents the middle mass and $w_b$ is the base displacement.

The total mass per unit length of the beam m is:

$$m = \rho_s A_s + 2\rho_p A_p \quad (8)$$

where the density of the substrate and the piezoelectric patches are $\rho_s$ and $\rho_p$. The cross section of the substrate and the piezoelectric layers are $A_s$ and $A_p$. The equivalent axial stiffness, $K_{eq}$ is:

$$K_{eq} = \frac{E_s A_s + 2E_p A_p}{L} \quad (9)$$

Where $E_s$ and $E_p$ are the Young's modulus for the substrate and the piezoelectric layers. L is the length of the beam. The piezoelectric coupling coefficient for parallel connection can be written as:

$$\alpha = -2\int_{\frac{h_s}{2}}^{h_p + \frac{h_s}{2}} e_{31}\frac{b}{h_p}z\,dz = -2be_{21}\frac{h_p + h_s}{2} \quad (10)$$

where $h_s$ and $h_p$ are the thickness of the substrate and the piezoelectric layer, $e_{31}$ is the piezoelectric coefficient, b is the width of the beam. We assume the free vibration mode shapes for this problem. In order to find the free vibration mode shapes, we solve the free vibration governing equation of a beam with mass in the middle:

$$\rho A \frac{\partial^2 w_{rel}}{\partial t^2} + EI \frac{\partial^4 w_{rel}}{\partial x^4} = 0 \quad (11)$$

The free vibration mode shape can be found using separation of variables. The vibration mode shape is a summation of all the modes:

$$w_{rel}(x, t) = \sum_{j=1}^{\infty} \phi_j(x) T_j(t) \quad (12)$$

where $\phi_i$ is the spatial term and $T_1$ is the temporal term of the jth mode shape. In the present embodiment, the beam is buckled on its first mode. Thus, we only consider the first free vibration mode shape for our energy harvester (only j=1).

Since there is a mass in the middle of the beam, we assume two sections for the beam, section one (the section on the left side of the mass) and section two (the section on the right side of the mass). The general solution for the spatial part of equation (equation (12)) can be written as:

$$\phi_i(x) = a_{i1}\sin\left(\frac{\beta}{\sqrt{C}}x\right) + a_{i2}\cos\left(\frac{\beta}{\sqrt{C}}x\right) + a_{i3}\sinh\left(\frac{\beta}{\sqrt{C}}x\right) + a_{i4}\cosh\left(\frac{\beta}{\sqrt{C}}x\right) \quad (13)$$

where, $\phi_i$ is the spatial term of the first mode of the ith section of the beam (i=1,2). $a_{i1}$, $a_{i2}$, $a_{i3}$, $a_{i4}$, and β are calculated using the boundary, continuity, and equilibrium conditions, and C is Singiresu S Rao, Vibration of continuous systems:

$$C = \sqrt{\frac{EI}{\rho A}} \quad (14)$$

The natural frequency of the first vibration mode and the eight unknown coefficients of the spatial term ($\alpha_{11}$, $\alpha_{12}, \ldots, \alpha_{23}, \alpha_{24}$) were found using known methods. Using the boundary conditions at the clamped ends (zero deflection and zero slope) and the equilibrium and continuity conditions at the middle of the beam we have:

$$\begin{cases} \phi_1(0) = 0 \\ \phi_1'(0) = 0 \\ \phi_2(L) = 0 \\ \phi_2'(L) = 0 \\ \phi_1\left(\frac{L}{2}\right) = \phi_2\left(\frac{L}{2}\right) \\ \phi_1'\left(\frac{L}{2}\right) = \phi_2'\left(\frac{L}{2}\right) \\ \phi_1''\left(\frac{L}{2}\right) = \phi_2''\left(\frac{L}{2}\right) \\ EI\phi_1^{(3)}\left(\frac{L}{2}\right) + M_{mid}\omega^2 \phi_1\left(\frac{L}{2}\right) = EI\phi_2^{(3)}\left(\frac{L}{2}\right) \end{cases} \quad (15)$$

The natural frequency ($\omega$) is:

$$\omega = \beta^2 \quad (16)$$

After finding the coefficients we mass normalize them as:

$$M_{mid}\phi_1^2\left(\frac{L}{2}\right) + \rho A \left( \int_0^{\frac{L}{2}} \phi_1^2 dx + \int_{\frac{L}{2}}^L \phi_2^2 dx \right) = 1 \quad (17)$$

If we multiply equation (7) by the mass normalized mode shape and integral on the length of the beam, we will have:

$$M\ddot{T} + c\dot{T} + (K+p)T + NT^3 + \chi V(t) = \gamma \ddot{w}_b \quad (18)$$

where M is the modal mass. As mentioned above, the amplitude of the mode shapes are chosen such that the modal mass equals one—i.e., the mass normalized mode shapes are used. c is the damping ratio, K stands for the linear stiffness, the reduction of the stiffness coefficient due to the axial force is p, N is the nonlinear coefficient, and the coupling coefficient is $\chi$:

$$\begin{cases} M = m \int_0^L \phi^2(x) dx \\ K = EI \int_0^L \phi^{(4)}(x)\phi(x) dx \\ p = (P_c + K_{eq}\Delta) \int_0^L \phi''(x)\phi(x) dx \\ N = -\frac{K_{eq}}{2} \int_0^L \phi'^2(x) dx \int_0^L \phi''(x)\phi(x) dx \\ \chi = 2\alpha \left[ \left(\phi'\left(\frac{L}{4}\right) - \phi'(0)\right) + \left(\phi'\left(\frac{L}{4}\right) - \phi'(L)\right) \right] \\ \gamma = M_{mid}\phi_1\left(\frac{L}{2}\right) + m \int_0^L \phi dx \end{cases} \quad (19)$$

The piezoelectric patches are connected in parallel. By using the Kirchhoff's current law for the electrical governing equation, we have:

$$C_p \dot{V} + \frac{V}{R_1} = -\chi \dot{T} \quad (20)$$

where $R_1$ is the shunt resistor and $c_p$ is the internal capacitance for the piezoelectric layer. For the two piezoelectrics in parallel, the capacitance is:

$$C_p = 2\epsilon_{33}^s \frac{Lb}{h_p} \quad (21)$$

In the above equation $\epsilon_{33}^s$ is the permittivity at constant stress. Equation (18) and equation (20) are the two coupled governing equations of the system:

$$\begin{cases} \ddot{T} + c\dot{T} + (K+p)T + NT^3 + \chi V(t) = \gamma \ddot{w}_b \\ C_p \dot{V} + \frac{V}{R_1} = -\chi \dot{T} \end{cases} \quad (22)$$

In the next section, we find the mode shape of a case study and solve the governing equations using the heartbeat vibrations as the base acceleration of the EN.

Supplemental Example

This supplemental example is fully a part of the foregoing specification. We assume a beam with brass substrate and four piezoelectric patches on each side. In order to prevent any charge cancellation, four piezoelectric patches are used on each side instead of one patch. For the substrate, we use 0.01 cm thick brass sheets. PSI-5A4E PZT sheets from PIEZO SYSTEMS, INC. are used as the piezoelectric element. The thicknesses of the piezoelectric layers are 0.01 cm. The bimorph beam is 2 cm long and 0.5 cm wide. A 10 g platinum mass is used in the middle of the beam as the middle mass to reduce the natural frequency. Both sides of the beam are clamped inside the outer frame.

Figure 15:
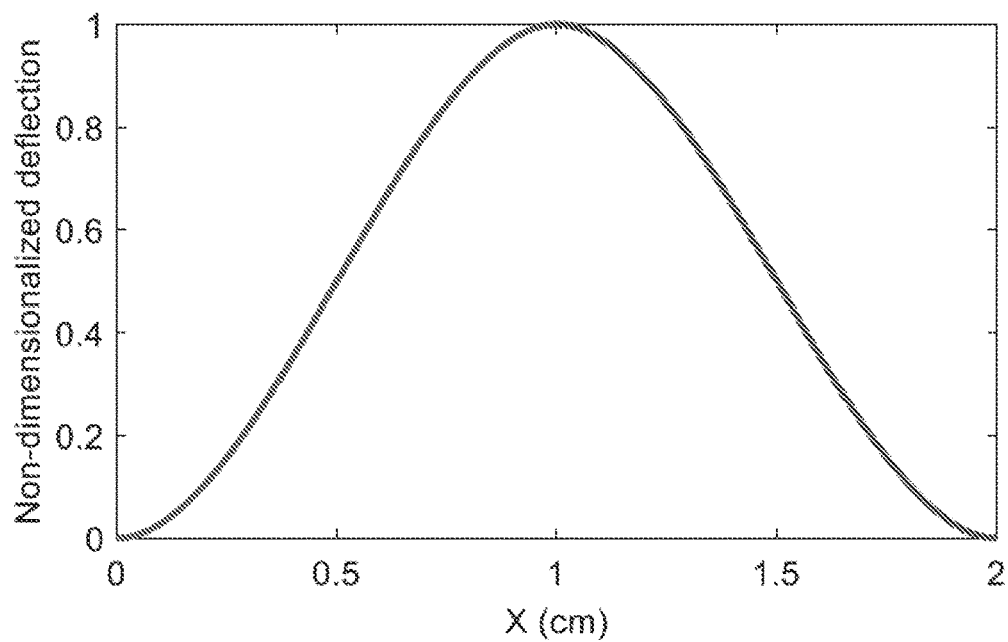
FIG. 15 is a graph showing the first buckling mode shape of the active beam.

First, we find the first buckled natural frequency and mode shape. $\Delta$ is assumed to be 0.1 μm. After the beam starts to buckle, the lower the $\Delta$ the lower the buckled natural frequency. Using the conditions in equation (15), we find the first natural frequency as 26.06 Hz. This frequency is much lower than the natural frequency of the beam before the buckling (210.68 Hz). FIG. 15 shows the first mode shape of the structure. We consider two safety factors for our device. One is the axial safety factor caused by the axial buckling force over the beam. The other one is the safety factor due to bending moment in the beam caused by the middle mass. Each of these safety factors are calculated for the substrate and the piezoelectric layer to avoid damage to the beam.

In order to test the output power for implantable biomedical devices, heartbeat vibrations were used as the base acceleration and the output power calculated. The generated power can be used to power lead-less pacemakers or other biomedical devices inside the body. The piezoelectric patches are connected in parallel. Having them in parallel keeps the voltage constant and adds their charges. Parallel configuration gives us the maximum power in this test shows the heartbeat acceleration in the time domain measured by Kanai.

Figure 16:
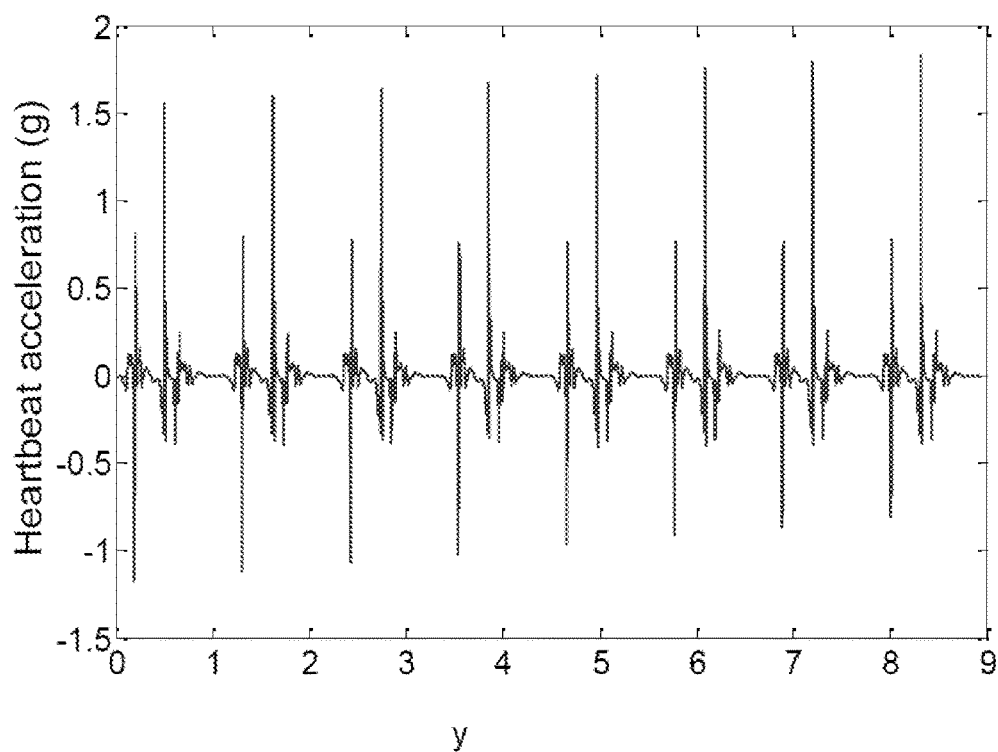
FIG. 16 is a graph showing heartbeat vibrations in the time domain.
Figure 17:
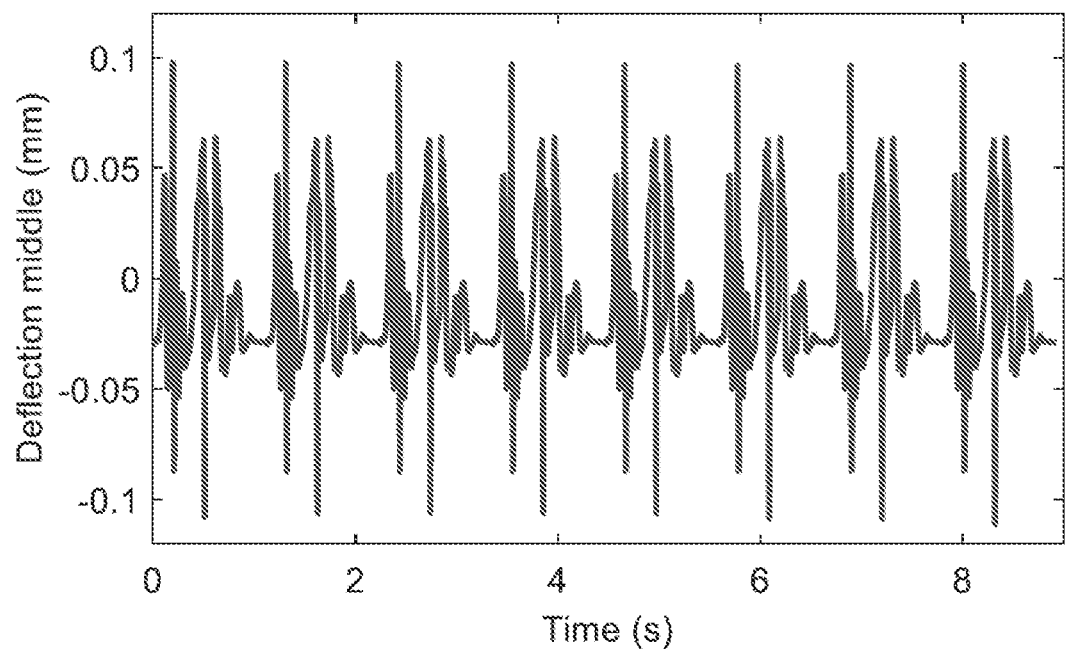
FIG. 17 is a graph showing deflection of the middle of the active beam due to heartbeat acceleration.

We solve the governing equations of the system with the vibrations shown in FIG. 16 as the base acceleration. After solving the equations, the temporal term of the deflection and the voltage across the resistor are calculated. FIG. 17 shows the deflection of the middle part of the beam due to the base acceleration. As it is shown in the figure, the beam vibrates around the buckled equilibrium point.

Figure 18:
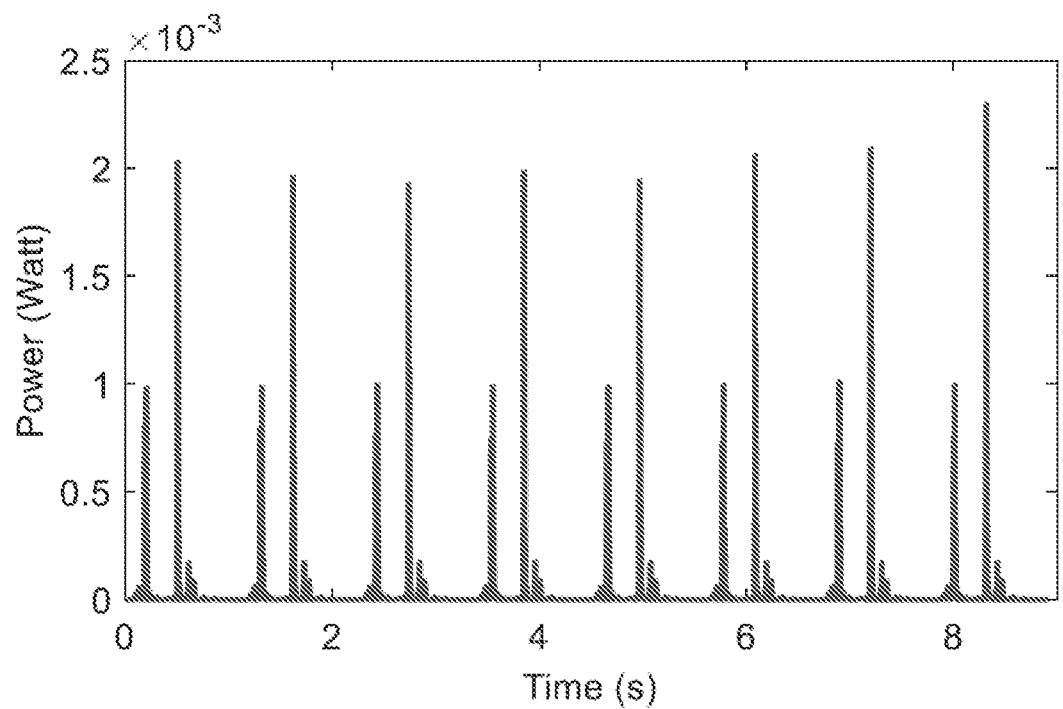
FIG. 18 is a graph showing instantaneous power of the EN from heartbeat vibrations.

FIG. 18 illustrates the instantaneous output power of the energy harvester in the time domain. The average power of the system is calculated as 26.96 µW which is sufficient to power a leadless pacemaker. A typical leadless pacemaker needs about 10 µW to operate. The shunt resistor is 48000 kΩ, which is calculated as $$R = \frac{1}{C_p \omega},$$

where $C_p$ is the capacitance of the two piezoelectric layers and ω is the natural frequency of the EN. For our EN, the internal capacitance for the two piezoelectric layers is 15.67 nF.

Figure 19:
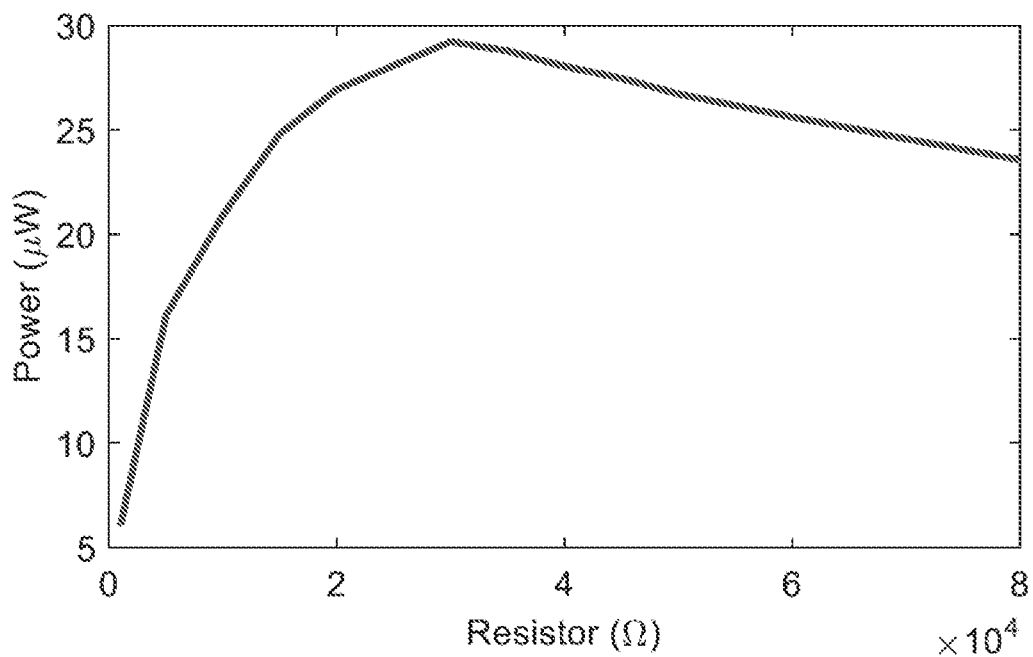
FIG. 19 is a graph showing the effect of the shunt resistor on the output power of the EN.

In order to find the maximum power, we do a resistor sweep test. FIG. 19 illustrates the effect of the shunt resistor on the output power. As predicted the maximum power happens at the vicinity of the resistor calculated from equation (10).

Figure 20:
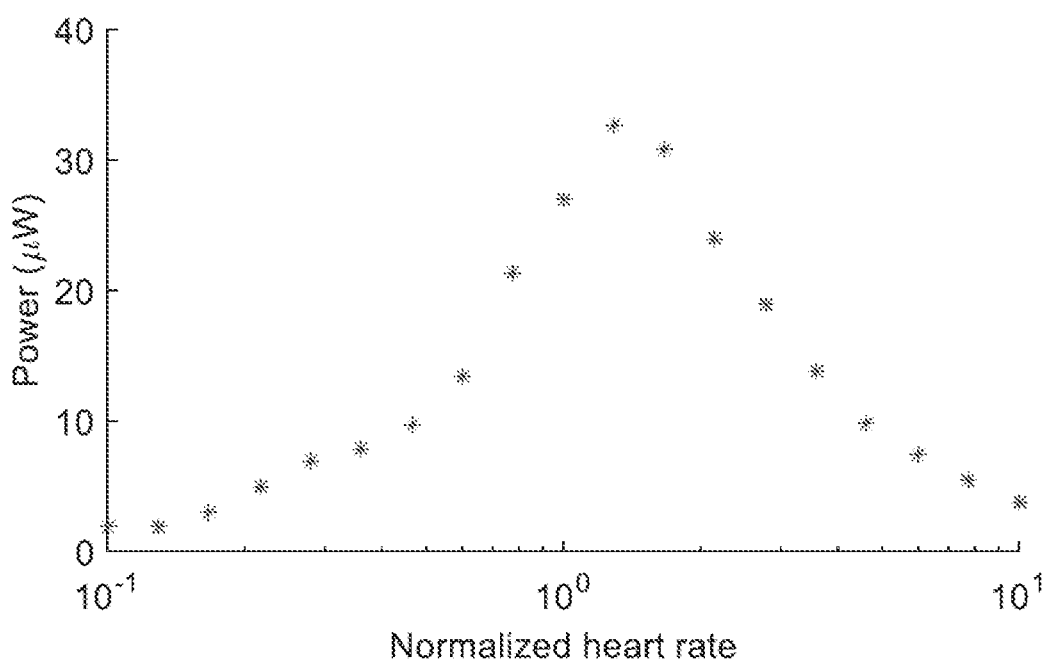
FIG. 20 is a graph showing output power of the EN for different heart rates.

FIG. 20 (output power of the EN for different heart rates) shows the effect of the heart rate on the output power. Since the device is nonlinear, it is robust to the heart rate changes. For a wide range (as low as ⅓ up to almost five times of a normal heartbeat), the generated power is sufficient for powering a pacemaker (10 µW). A normalized heart rate of 1 (10°) corresponds to 70 beats per minute. The EH is thus functional over the 25-350 bpm range of heart rate.

A nonlinear thermally buckled energy harvester was modeled in this example. A bimorph beam is buckled inside a rigid frame due to the difference in the coefficients of thermal expansion. The bimorph beam comprised a brass substrate and four piezoelectric patches covering each sides. The coupled governing equations of the system were derived and the mode shapes were calculated analytically. A mass was added to the middle of the beam to decrease the natural frequency of the system. Although the device is in a very small scale (1 cm³), the natural frequency is decreased to less than 30 Hz. The generated power can be used to power biomedical sensors and devices inside the body.

For a case study, it was shown that the EN can generate enough power to power a leadless pacemaker using the heartbeat vibrations. It was shown that the device is pretty robust to the change in the heart rates and generates sufficient power for powering a pacemaker over a wide range.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof

What is claimed is:

1. An energy harvester for harvesting energy from an external vibratory force, comprising:
   a frame having a base, a first side member affixed to the base, and a second side member affixed to the base and spaced apart from the first side member; and
   a first buckled beam coupled between the first side member of the frame and the second side member of the frame, the first buckled beam comprising:
   a substrate layer having a first end affixed to the first side member of the frame, a second end affixed to the second side member of the frame, a first face, a second face opposite to the first face, and a terminal for electrical connection to a load, the substrate being elastically deformable in response to the vibratory force;
   a first piezoelectric layer joined to the first face of the substrate layer and having a terminal for electrical connection to a load, the first piezoelectric layer comprising at least one piezoelectric patch; and
   wherein a coefficient of thermal expansion (CTE) of the frame differs from a CTE of the first beam to cause the first beam to be buckled.

2. The energy harvester of claim 1, wherein the first piezoelectric layer comprises four piezoelectric patches.

3. The energy harvester of claim 1, further comprising a second piezoelectric layer joined to the second face of the substrate layer, the second piezoelectric layer comprising at least one piezoelectric patch, wherein the second piezoelectric layer is electrically connected to the first piezoelectric layer.

4. The energy harvester of claim 3, wherein the first piezoelectric layer and the second piezoelectric layer are electrically connected in parallel.

5. The energy harvester of claim 4, wherein the first piezoelectric layer and the second piezoelectric layer each comprises four piezoelectric patches.

6. The energy harvester of claim 1, wherein the first beam further comprises a mass connected to the substrate layer to change the natural frequency of the first beam.

7. The energy harvester of claim 6, wherein the mass is connected to the substrate layer at a location substantially equidistant from the first end and the second end.

8. The energy harvester of claim 1, wherein the CTE of the frame is greater than the CTE of the first beam.

9. The energy harvester of claim 1, wherein the CTE of the frame differs from the CTE of the first beam according to $$T_{diff} = \frac{\Delta}{L(\alpha_f - \alpha_{eq})},$$

where $T_{diff}$ is a temperature difference, $\Delta$ is an axial displacement of the first beam due to thermal compression of the frame, L is a length of the first beam, $\alpha_f$ is the CTE of the frame, and $\alpha_{eq}$ is the CTE of the first beam.

10. The energy harvester of claim 1, further comprising a second buckled beam coupled between the first side member of the frame and the second side member of the frame, the second buckled beam comprising:
   a substrate layer having a first end affixed to the first side member of the frame, a second end affixed to the second side member of the frame, a first face, a second face opposite to the first face, and a terminal for electrical connection to a load, the substrate being elastically deformable in response to the vibratory force; and
   a first piezoelectric layer joined to the first face of the substrate layer and having a terminal for electrical connection to a load, the first piezoelectric layer comprising at least one piezoelectric patch.

11. The energy harvester of claim 1, wherein a length of the first beam is less than 2.5 cm.

12. The energy harvester of claim 11, wherein a length of the first beam is between 1 cm and 2 cm, inclusive.

13. The energy harvester of claim 1, wherein the first piezoelectric layer is electrically connected to the substrate layer.

14. The energy harvester of claim 13, wherein the piezoelectric layer is electrically connected to the substrate layer using a conductive epoxy.

15. The energy harvester of claim 1, wherein the first piezoelectric layer is joined to only a portion of a length of the substrate layer.

16. The energy harvester of claim 15, wherein the first piezoelectric layer is joined to a central portion of the length of the substrate layer.

17. The energy harvester of claim 1, wherein the first beam has a natural frequency which is substantially the same as a frequency of the applied vibratory force.

18. The energy harvester of claim 1, wherein the first beam has a natural frequency less than 35 Hz.

19. A method of making a buckled-beam energy harvester for harvesting energy at an operating temperature, comprising:

heating a frame to an assembly temperature, the frame having a first side member and a second side member spaced apart from the first side member, wherein the assembly temperature is higher than the operating temperature;

heating a beam to the assembly temperature, the beam having a first end, a second end, and a coefficient of thermal expansion (CTE) which is less than a CTE of the frame, wherein the beam comprises a substrate layer joined to a first piezoelectric layer;

affixing the first end of the beam to the first side member of the frame and the second end of the beam to a second side member of the frame to form an energy harvester assembly; and cooling the energy harvester assembly to the operating temperature to cause the beam to buckle.

* * * * *